(12) United States Patent
Suzuki

(10) Patent No.: US 6,944,267 B2
(45) Date of Patent: Sep. 13, 2005

(54) X-RAY IMAGE DIAGNOSTIC DEVICE, AND X-RAY IMAGE DATA CORRECTING METHOD

(75) Inventor: Katsumi Suzuki, Kashiwa (JP)

(73) Assignee: Hitachi Medical Corporation, Tokyo (JP)

(*) Notice: Subject to any disclaimer, the term of this patent is extended or adjusted under 35 U.S.C. 154(b) by 66 days.

(21) Appl. No.: 10/481,574

(22) PCT Filed: Jun. 21, 2002

(86) PCT No.: PCT/JP02/06221

§ 371 (c)(1),
(2), (4) Date: Dec. 22, 2003

(87) PCT Pub. No.: WO03/000136

PCT Pub. Date: Jan. 3, 2003

(65) Prior Publication Data

US 2004/0240612 A1 Dec. 2, 2004

(30) Foreign Application Priority Data

Jun. 22, 2001 (JP) ..................... 2001-190394

(51) Int. Cl.[7] .............................. H05G 1/64
(52) U.S. Cl. .................. 378/98.8; 250/252.1
(58) Field of Search .............. 378/98.8, 19, 62, 378/96, 207; 250/252.1, 370.09

(56) References Cited

U.S. PATENT DOCUMENTS 6,014,420 A * 1/2000 Ooi ................ 378/19
6,862,338 B2 * 3/2005 Kinno et al. ........... 378/98.8
2004/0155209 A1 * 8/2004 Struye et al. ........... 250/587

FOREIGN PATENT DOCUMENTS

| JP | 04-015048 | * | 1/1992 |
| JP | 08-117212 | * | 5/1996 |
| JP | 10-213667 | * | 8/1998 |
| JP | 2000-284058 | * | 10/2000 |
| JP | 2001-066368 | * | 3/2001 |

* cited by examiner

Primary Examiner—Edward J. Glick
Assistant Examiner—Jurie Yun
(74) Attorney, Agent, or Firm—Antonelli, Terry, Stout & Kraus, LLP

(57) ABSTRACT

An X-ray image diagnostic device of the invention has sensitivity-information-acquisition controlling means commanding synchronization between X-ray irradiation from the X-ray source and readout of X-ray plane detector for correcting sensitivity. When sensitivity information of the X-ray plane detector is calculated using the intensities of X-rays irradiated onto the X-ray plane detector and X-rays detected by the X-ray plane detector, readout of the X-ray plane detector is performed synchronously with X-ray irradiation, and sensitivity information corresponding to variation of the amount of X-ray radiation onto the X-ray plane detector during the reading time is determined using data of every readout channel. Therefore, sensitivity information enabling an accurate sensitivity correction can be obtained from a single output image. This sensitivity information is stored in sensitivity-information-storing means and used for correcting sensitivity of X-ray image data acquired in actual measurements.

8 Claims, 5 Drawing Sheets

X-RAY IMAGE DIAGNOSTIC DEVICE, AND X-RAY IMAGE DATA CORRECTING METHOD

FIELD OF THE INVENTION

The present invention relates to an X-ray image diagnostic device using an X-ray plane detector. Particularly, it relates to an X-ray image diagnostic device having a function of correcting sensitivity to X-ray energy of an X-ray plane detector exposed to X-rays.

RELATED ART

Conventional X-ray image diagnostic devices are constructed such that an X-ray image output from an X-ray plane detector resulting from irradiation of X-rays onto an object is displayed on a TV monitor or the like.

An ordinary X-ray plane detector consists of scintillators that convert X-rays transmitted through an object to light and photodiodes that convert the light output from the scintillators to electric charge. Detecting devices, each of which consists of a scintillator and a photodiode, are arranged in a matrix corresponding to the individual pixels. Electric charge converted from light by each photodiode is read out via a switching device such as a thin film transistor (TFT) to produce an X-ray image.

Sensitivity differs among the detectors due to difference in the characteristics of the individual scintillators and photodiodes composing the detector. Accordingly, it is necessary to deteremine sensitivity information for each detector in advance and to correct detected signals using the sensitivity information upon imaging.

Conventionally, such sensitivity correction is carried out by irradiating X-rays of a predetermined intensity onto the X-ray plane detector with no object present to output an image from the X-ray plane detector and determining detector sensitivity information from the image. The sensitivity information determined using the X-rays of the predetermined intensity is also used when X-rays of a different intensity from the predetermined intensity are irradiated onto an object to carry out imaging. This causes a problem in that sensitivity correction is not accurate.

In order to solve this problem, X-rays need to be irradiated multiple times to find the sensitivities for X-rays of various intensities. This causes another problem in that the work of the operator for collecting sensitivity information increases and that the capacity of the storage medium for storing the collected sensitivity information must be increased.

Therefore, an object of the present invention is to provide an X-ray image diagnostic device capable of obtaining sensitivity information for various X-ray intensities from a single output image and performing accurate sensitivity correction.

DISCLOSURE OF THE INVENTION

To attain the above-mentioned object, an X-ray image diagnostic device of the present invention comprises an X-ray source for irradiating X-rays onto an object to be imaged, an X-ray plane detector placed face to face with the X-ray source for outputting X-rays transmitted through the object as X-ray image data, image storage means for storing the X-ray image data output from the X-ray plane detector as digital data, and sensitivity correcting means for performing sensitivity correction of the X-ray image data stored in the image storage means, wherein said sensitivity correcting means comprises sensitivity-information-acquisition controlling means for commanding synchronization of irradiation of X-rays from the X-ray source and readout of X-ray image data from the X-ray plane detector, sensitivity-information calculating means for calculating sensitivities of plural readout channels of the X-ray plane detector using the X-ray image data read out synchronously with X-ray irradiation, and sensitivity-information storing means for storing the sensitivity information calculated by the calculating means.

By synchronizing irradiation of X-rays from the X-ray source with readout of X-ray image data from the X-ray plane detector and calculating sensitivity information for each readout channel based on the X-ray image data, sensitivity information corresponding to change in the amount of X-ray radiation irradiated onto the X-ray plane detector within the read time can be found. That is, sensitivity information enabling accurate sensitivity correction can be obtained from a single output image.

The control for synchronizing X-ray irradiation with readout of X-ray image data performed by the sensitivity-information-acquisition controlling means includes not only that for performing X-ray irradiation and readout of X-ray image data at the same time but also that for performing readout of X-ray image data at a desired time points synchronized with the X-ray irradiation.

BEST MODE FOR CARRYING OUT THE PRESENT INVENTION

Embodiments of the X-ray image diagnostic device of the present invention will be explained with the reference to the attached drawings.

Figure 1:
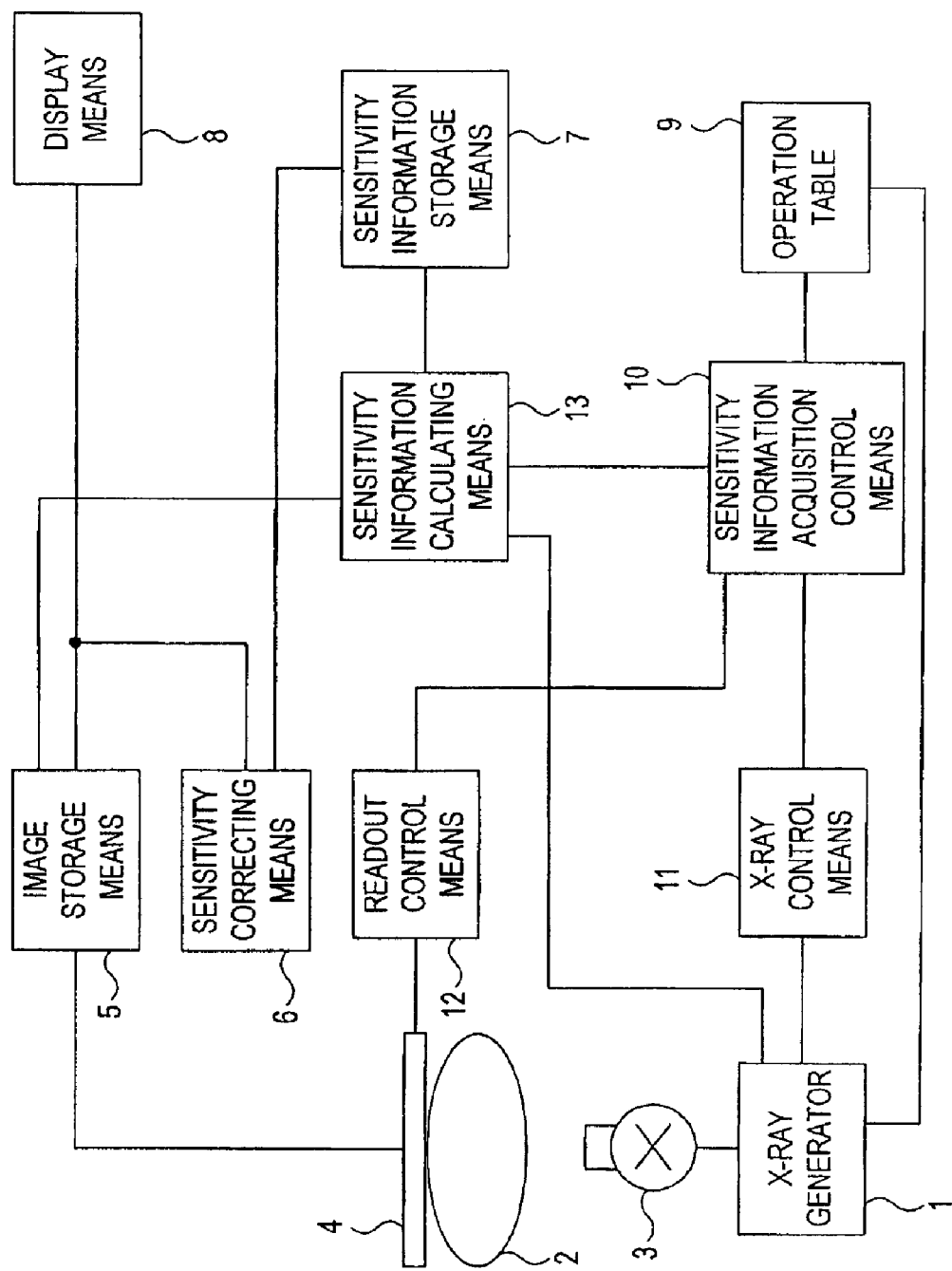
FIG. 1 is a functional diagram showing the X-ray image diagnostic device of the present invention.

FIG. 1 is a functional diagram showing the X-ray image diagnostic device of the present invention.

As shown in FIG. 1, the X-ray image diagnostic device of the present invention has an X-ray source 3 which irradiates X-rays onto an object 2 to be imaged under the control of an X-ray generator 1, and an X-ray plane detector which is placed face to face with the X-ray source 3 and outputs transmitted X-rays through the object 2 as X-ray image data. The X-ray image diagnostic device further comprises means for displaying X-ray image data output from the X-ray plane detector 4 as images (5–8), control means for controlling X-ray irradiation and image-signal readout from the X-ray plane detector 4 (10,11,12), and an operation table 9 for inputting directions and conditions necessary for operation of the device etc.

The X-ray generator 1 is connected to the X-ray control means 11 and controls the X-ray source 3 to irradiate X-rays having a desired X-ray intensity at desired times according to control signals from the control means 11.

Figure 2:
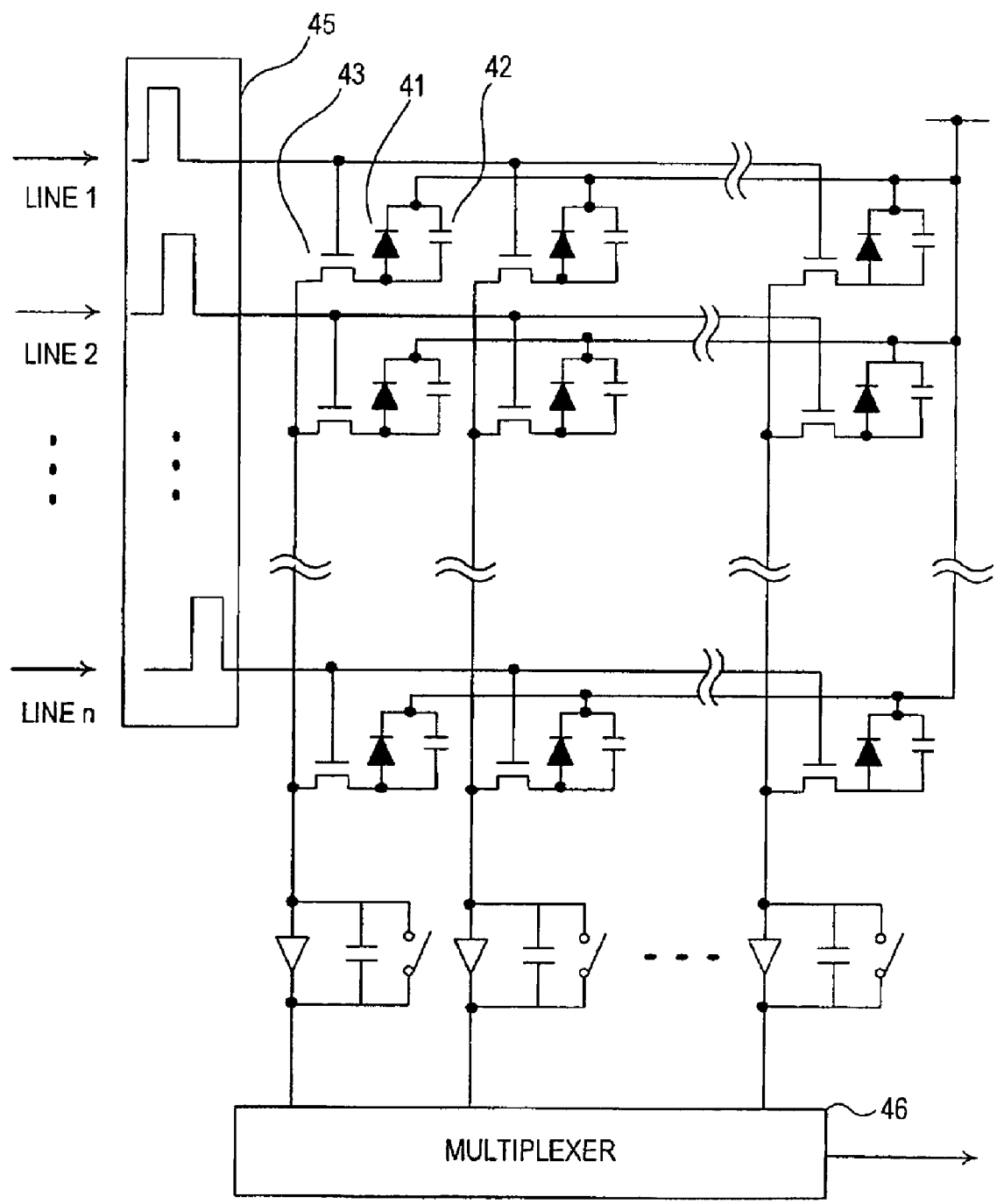
FIG. 2 shows a configuration of an X-ray plane detector.

The X-ray plane detector 4 consists of scintillators which convert the X-rays transmitted through the object to light and sensor cells which convert light generated by the scintillators to electric signals. As shown in FIG. 2, a large numbers of sensor cells are arranged in a matrix. Each sensor cell constitutes one pixel. Each sensor cell comprises a photodiode 41 which converts light output from the scintillator to electric charge, a capacitor 42 which stores the electric charge, and a switching device 43 (thin film transistor :TFT) which reads the stored electric charge. The combination of the scintillator and photodiode can be replaced by a sensor cell of direct conversion type which converts X-ray to electric charge directly.

The gate terminal of the switching device 43 is connected through a common line to an associated line output terminal of the gate driver 45. The gate driver 45 is connected to the readout control means 12 (FIG. 1) that controls reading of signals from the X-ray plane detector 4. The drain terminals of the switching devices 43 in the same column are connected in common through integration circuit to an associated input terminal of multiplexer 46.

When X-rays are irradiated onto the X-ray plane detector 4, the photodiodes 41 store electric charges in the capacitors 42 in proportion to the amount of radiation. The stored electric charge signals are read by operating the TFTs 43. During this operation, the multiplexer 46 reads one by one in a temporal order the signals input to the input terminal during the period of a single pulse output from each line output terminal of the gate driver 45. Thus, electric charges stored for every pixel of one line are read as an image signal. When reading of one line is completed, reading of the next line is started. Thus, the electric charges for every line are read out in order.

Means (5–8) for displaying X-ray image data output from the X-ray plane detector 4 comprise image storage means 5, sensitivity correcting means 6, sensitivity-information storage means 7, and displaying means 8. The image storage means 5 stores X-ray image data output from the X-ray plane detector 4 as digital data, as mentioned above, and outputs the digital data to the displaying device 8. The sensitivity correcting means 6 performs sensitivity correction of the X-ray image data stored in the image storage means 5 using sensitivity information acquired and stored in the sensitivity-information storage means 7 beforehand. The manner of obtaining the sensitivity information will be explained later. X-ray image data corrected by the sensitivity correction is also stored in the image storage means 5. The X-ray image data stored in the image storage means 5 both before and after the correction are displayed on the displaying means 8 as images.

In order to acquire the sensitivity information used in the sensitivity correcting means 6, the X-ray image diagnostic device according to this embodiment further comprises sensitivity-information-acquisition control means 10 which controls the X-ray control means 11 and readout control means 12 so as to operate synchronously, and sensitivity-information calculating means 13 which calculates the sensitivity information using image data obtained by the X-ray plane detector 4 controlled by the sensitivity-information-acquisition control means 10. The sensitivity information calculated by the sensitivity-information calculating means 13 is stored in the sensitivity-information storage means 7 for use in correction processing by the sensitivity correcting means 6.

The sensitivity-information-acquisition control means 10 operates and drives the X-ray control means 11 and readout control means 12 according to the operator's directions input from the operation table 9 in order to acquire the sensitivity information. The readout control means 12 operates according to directions from the sensitivity-information-acquisition control means 10 and controls the X-ray plane detector 4 so that X-ray image data is read from the X-ray plane detector 4 at a desired time synchronous with X-ray irradiation. The X-ray image data read under the control of the readout control means 12 is temporally stored in the image storage means 5. The sensitivity-information calculating means 13 reads out the X-ray image data for sensitivity information stored in the image storage means 5, calculates sensitivity information for each readout channel of the X-ray plane detector 4, and stores it in the sensitivity-information storage means 7.

Next, operation of the X-ray image diagnostic device of this embodiment will be explained.

The procedure for acquiring sensitivity information will be explained first. Acquisition of sensitivity information is started by sending a signal for starting acquisition of sensitivity information from the operation table 9 to the sensitivity-information-acquisition control means 10 when no object 2 is present.

Upon receiving the starting signal, the sensitivity-information-acquisition control means 10 sends a signal for starting of X-ray image data readout to the readout control means 12 and at the same time sends an X-ray irradiation start signal to the X-ray control means 11. When the X-ray generator 1 receives the X-ray irradiation start signal, it controls the X-ray source 3 so as to irradiate X-rays of a desired intensity onto the X-ray plane detector 4. The desired intensity of the X-rays irradiated onto the X-ray plane detector 4 is an intensity capable of obtaining a sufficient amount of sensitivity information for sensitivity correction carried out by the sensitivity correcting means 6 and may be set to a constant value beforehand or may be varied by sending the operator's directions through the operation table 9 directly to the X-ray generator 1.

Figure 3:
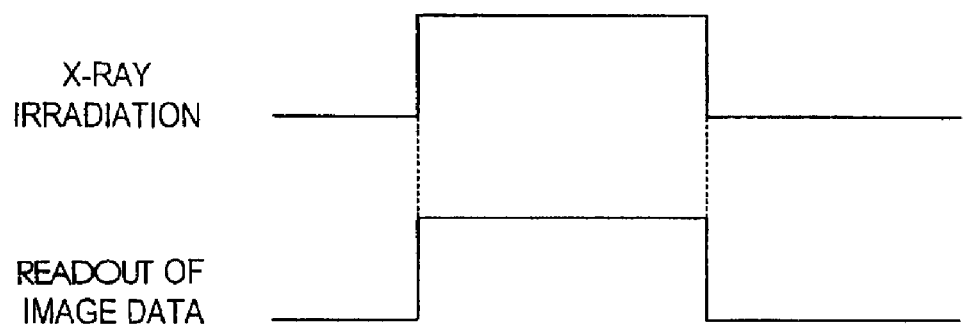
FIG. 3 is a timing chart of X-ray irradiation onto the X-ray plane detector and readout of X-ray image data from the X-ray plane detector.

FIG. 3 is a timing chart illustrating the timing of X-ray irradiation onto the X-ray plane detector 4 by the X-ray source 3 and reading of X-ray image data from the X-ray plane detector 4.

Figure 4:
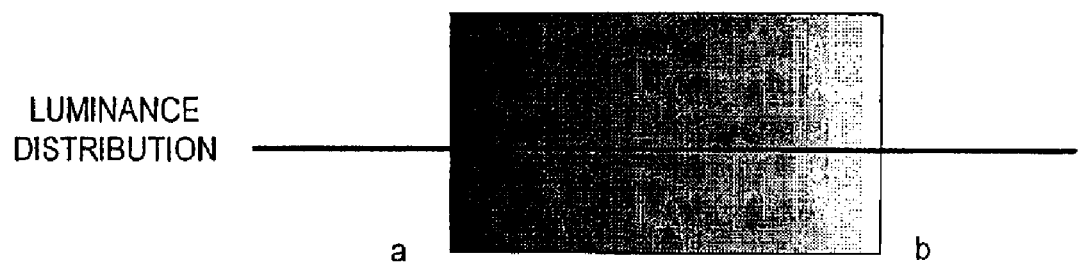
FIG. 4 is a view of schematically illustrating X-ray image data stored in image storage means 5 when the X-ray image data is read out from the X-ray plane detector according to the timing chart of FIG. 3.
Figure 5:
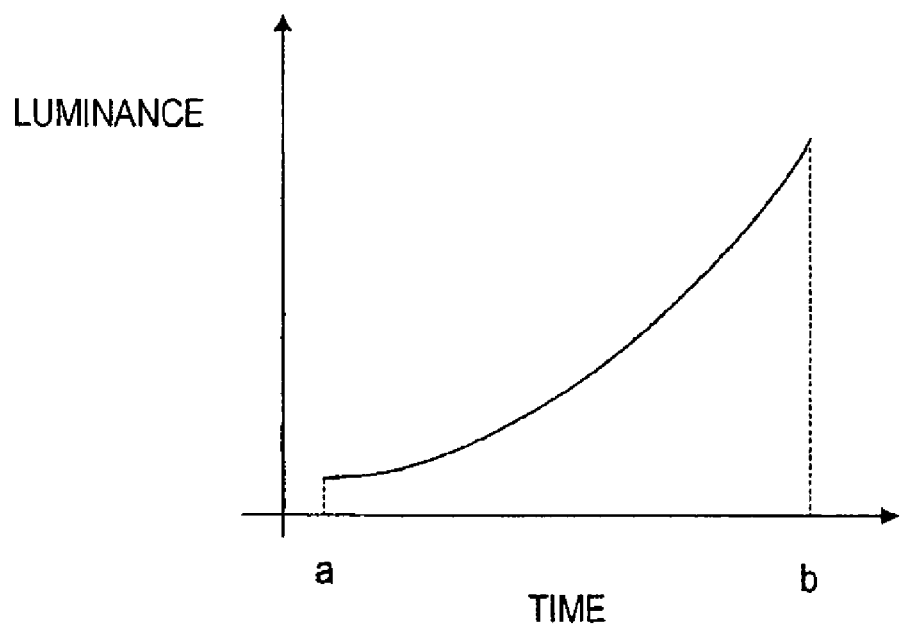
FIG. 5 is a graph showing a luminance distribution between arbitrarily selected channels (a) and (b) on a line of the X-ray image data.

As shown in the figure, reading of X-ray image data is started at the same time as irradiation of X-rays onto the X-ray plane detector 4. The X-ray image data read from the X-ray plane detector 4 by the readout control means 12 is stored in the image storage means 5. The X-ray image data stored in the image storage means 5 and the luminance distribution thereof are shown in FIG. 4 and FIG. 5. As illustrated, the luminance distribution changes between arbitrarily selected readout channels (a) and (b) on the same line.

As shown in FIG. 3, since reading of X-ray image data from the X-ray plane detector 4 begins at the same time as the X-ray source 3 begins to irradiate X-rays onto the X-ray plane detector 4, a pixel at the point (a), which is detected soon after the X-ray irradiation, is not exposed to a sufficient amount of X-ray radiation. On the other hand, a pixel at the point (b) is exposed to X-rays during the period from the beginning of the X-ray irradiation (beginning of reading) to the reading of X-ray image data of the pixel at the point (b) As the result, the luminance distribution between (a) and (b) comes to have the shape shown in FIG. 5.

The abscissa of the graph shown in FIG. 5 corresponds to the amount of X-ray radiation input to each pixel and therefore the sensitivities to various X-ray intensities between readout channels (a) and (b) can be obtained. That is, by determining the luminance distribution curve between (a) and (b) of the X-ray image data, it is possible to produce sensitivity information of readout channels for reading image data between (a) and (b) of the X-ray plane detector 4. In the same manner, sensitivity information for all of the readout channels of the X-ray plane detector 4 to various incident X-ray intensities can be produced by determining luminance curves of the X-ray image stored in the data image storage means 5 in all of the readout channel directions.

Although FIGS. 4 and 5 show that sensitivity information between two points on one line defined arbitrarily is read, the point (a) from which readout of sensitivity information is started and the point (b) where readout is terminated need not be on the same line but can be any points on the X-ray plane detector 4, because readout of X-ray image data from the X-ray plane detector 4 is carried out for each line in order as explained with reference to FIG. 2. Thus, sensitivity information for various X-ray intensities corresponding to change of the X-ray exposure time of these detecting devices between these two points can be obtained.

The sensitivity information for each readout channel of the X-ray plane detector 4 calculated by the sensitivity information calculating means 13 can be expressed by the equation $S(i,k)=Q/I(i,k)$. Here, S represents X-ray sensitivity [C/J], Q represents electric charge density generated in one unit-area of the photodiode, I represents intensity [J/m$^2$] of an incident X-ray, i is the channel number on one line and k is the column number. Thus, sensitivity to incident X-ray intensities $I(1,1)$ ... $I(x,y)$ (x,y is the matrix size) varying between X-ray readout channels can be calculated.

The sensitivity information for each readout channel of the X-ray plane detector 4 thus calculated by the sensitivity information calculating means 13 is stored in sensitivity information storage means 7 and used by the sensitivity correcting means 6 for sensitivity correction of the X-ray image data.

Specifically, when X-rays of a predetermined intensity is irradiated onto an object 2 and the obtained X-ray image data is subjected to the sensitivity correction using the sensitivity S for the intensity of the irradiated X-rays, the detected X-ray intensity D' is corrected according to the following equation:

$$D''=D'\times S$$

D': Electric charge density generated in one unit-area of photodiode [C/m$^2$]
D": Corrected X-ray intensity [J/m$^2$]
S: X-ray sensitivity [C/J]

If no sensitivity information is available for the actual intensity of the irradiated X-rays, it is possible to use a value interpolated from two points of sensitivity information for larger and smaller X-ray intensities.

While sensitivity information for all channels from the beginning to the end of the reading of the X-ray image data is calculated in this embodiment, sensitivity information for a plurality, but not all of the channels, can be calculated and sensitivity information between these channels be found by interpolation.

According to this embodiment, sensitivity information for various X-ray intensities can be obtained by starting X-ray image data readout from the X-ray plane detector 4 at the same time as irradiating X-rays onto the X-ray plane detector 4 and determining sensitivity information from the detected X-ray intensity for each pixel.

The above embodiment was explained with regard to the case where the readout of X-ray image data from the X-ray plane detector 4 is started at the same time as irradiating X-rays onto the X-ray plane detector 4. However, as known in the art, it takes a certain amount of time from the start of X-ray irradiation to achieve a desired X-ray intensity. A control considering this X-ray rise characteristic is necessary. Hereinafter, a method of acquiring sensitivity information for each readout channel of the X-ray plane detector 4 taking the rise characteristic into account will be explained taking as an example an X-ray plane detector 4 having an image-readout number of 30 images per second.

Figure 6:
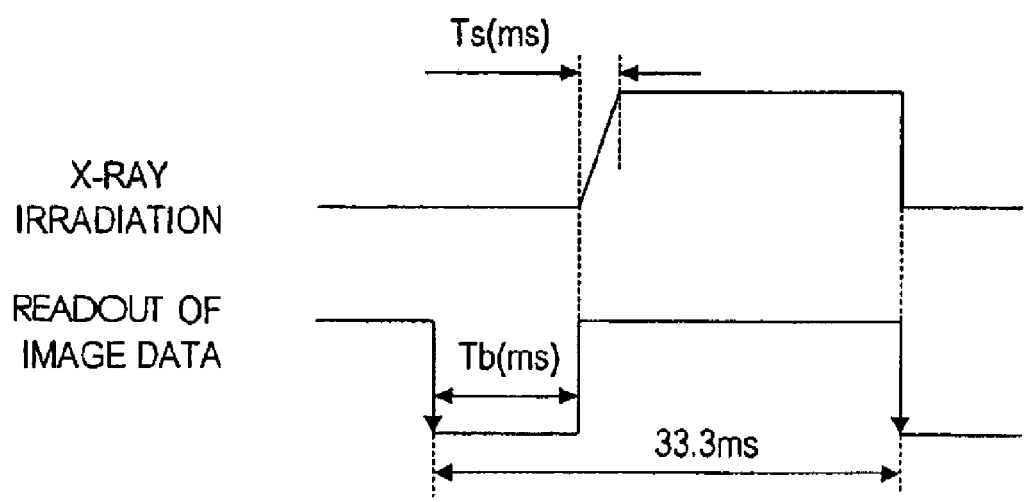
FIG. 6 shows a timing chart of X-ray irradiation onto an X-ray plane detector 4 having a specific X-ray rise characteristic and of X-ray image data read out from the X-ray plane detector 4.

FIG. 6 is a timing chart of X-ray irradiation onto the X-ray plane detector 4 having an X-ray rise characteristic and reading of X-ray image data from the X-ray plane detector 4.

When irradiation of X-rays onto the X-ray plane detector 4 is started, the sensitivity-information calculating means 13 obtains X-ray waveform-information from the X-ray generator 1 and calculates the rise time of the X-rays ($T_s$ in FIG. 6) using the waveform-information. The sensitivity-information calculating means 13 determines image data, which is read from the X-ray plane detector 4 within the rise time ($T_s$) of the X-ray, among X-ray image data stored in the image storage means 5. Specifically, when the number of image readouts from the X-ray plane detector 4 is 30 images per second, the time required to read one image is 33.3 ms. Defining the blanking time, i.e., the time within this period when only X-ray irradiation is carried out and X-ray image data is not read, as $T_b$, the time Tr required solely for reading X-ray image data becomes:

$$T_r = 33.3 - T_b \tag{1}$$

If the number of pixels of X-ray image data read from the X-ray plane detector 4 is (x×y), the time $T_p$ required for reading one pixel becomes:

$$T_p = (33.3 - T_b)/(x \times y) \tag{2}$$

Pixels which are read within a time satisfying the following condition from the beginning of reading of the X-ray image data are pixels which are read within the X-ray rise time ($T_s$).

$$T_s \geq T_p \times n (n=0,1,2 \ldots) \tag{3}$$

The sensitivity-information calculating means 13 calculates sensitivity information for each readout channel of the X-ray plane detector 4 from X-ray image data read by the X-ray plane detector 4 after the time satisfying the above equation and stores it in the sensitivity information storage means 7. Image data within the X-ray rise time which was not obtained, that is, sensitivity information within the time, can be found using the sensitivity information found from image data after the rise time and stored in the sensitivity information storage means 7, by extrapolation using for example a multinomial approximation method.

While the case where the X-ray waveform has a rise characteristic was explained in the embodiment shown in FIG. 6, the X-ray waveform generated by the X-ray generator 1 is generally known to have not only a rise characteristic but also a fall characteristic. For dealing with such a characteristic, the same process as used for the rise characteristic can be applied to obtain sensitivity information for each readout channel of the X-ray plane detector 4 while avoiding the influence of the fall characteristic.

Although X-ray image data detected during the rise time or fall time is not used for calculating sensitivity information in the above embodiment, a delay time corresponding to the rise time may be set for the sensitivity-information-acquisition control means 10 to control the readout control means 12 and the X-ray control means 11.

Figure 7:
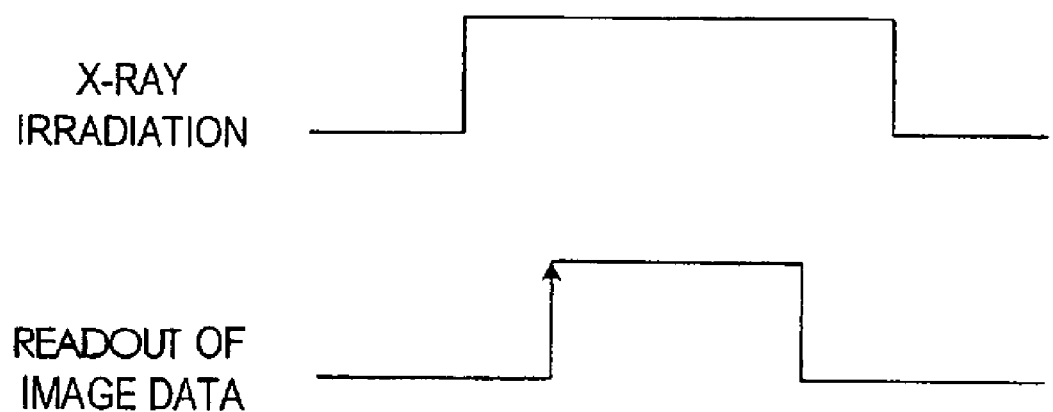
FIG. 7 shows another exemplary timing chart of X-ray irradiation onto the X-ray plane detector and X-ray image data read out from the X-ray plane detector.

Such an embodiment is shown in FIG. 7. FIG. 7 is a timing chart of X-ray irradiation onto the X-ray plane detector and of X-ray image data readout from the X-ray plane detector.

In this embodiment, as illustrated, reading of X-ray image data from the X-ray plane detector 4 is started at a predetermined time after the start of X-ray irradiation and terminated a predetermined time before the termination of X-ray irradiation. In this embodiment, X-ray image data is not read during the X-ray rise time and fall time. The times corresponding to the rise and fall of the X-ray waveform can be set using the X-ray waveform obtained from the X-ray generator 1 as in the embodiment shown in FIG. 6

The method of synchronizing the reading of X-ray image data with the irradiation of X-rays is not limited to that of the embodiments shown in FIGS. 3 and 6 but the delay time between X-ray irradiation and X-ray image data reading or the reading time can be set arbitrary. In this case, the luminance distribution (sensitivity information) of an arbitrary range of the X-ray intensity can be obtained.

As explained above, according to the X-ray image diagnostic device of present invention, sensitivity information for performing accurate sensitivity correction can be obtained from a single output image. The operator's work for collecting sensitivity information can therefore be reduced and increase in the capacity of a storage medium for storing the sensitivity information can be minimized.

What is claimed is:

1. An X-ray image diagnostic device comprising an X-ray source for irradiating X-rays onto an object to be examined, an X-ray plane detector placed opposite to the X-ray source for outputting X-ray image data corresponding to X-rays transmitted through the object, image storage means for storing the X-ray image data output from the X-ray plane detector as digital data, and sensitivity correcting means for performing sensitivity correction on the X-ray image data stored in the image storage means, wherein said sensitivity correcting means comprises sensitivity-information-acquisition controlling means for commanding that X-ray irradiation from said X-ray source be synchronized with readout of the X-ray image data from the X-ray plane detector, sensitivity-information calculating means for calculating sensitivity information for a plurality of readout channels of the X-ray plane detector using the X-ray image data read out synchronously with X-ray irradiation, and sensitivity-information storage means for storing the sensitivity information calculated by the calculating means.

2. The X-ray image diagnostic device of claim 1, wherein said sensitivity-information calculating means calculates the sensitivity information using X-ray image data other than data detected during the rise time and fall time of irradiated X-rays.

3. The X-ray image diagnostic device of claim 1, wherein said sensitivity-information-acquisition controlling means controls the X-ray plane detector such that the X-ray image data are read out at a predetermined time synchronously with X-ray irradiation.

4. The X-ray image diagnostic device of claim 1, wherein said sensitivity-information-acquisition controlling means sets a delay time corresponding to the rise time of the irradiated X-rays for reading out the X-ray image data.

5. The X-ray image diagnostic device of claim 1, wherein said sensitivity correcting means performs sensitivity correction using a value obtained by interpolating from sensitivity information for at least two points of a plurality of readout channels calculated by said sensitivity information calculating means.

6. The X-ray image diagnostic device of claim 1, wherein said sensitivity-information-acquisition controlling means determines X-ray image data readout timing based on X-ray waveform information obtained from the X-ray source.

7. A method of correcting X-ray image data transmitted through an object to be examined and detected by an X-ray plane detector by calculating sensitivity information for readout channels of the X-ray plane detector using the intensities of irradiated X-rays and of detected X-rays and using the sensitivity information, wherein readout of the X-ray plane detector is performed synchronously with X-ray irradiation and sensitivity information corresponding to variation of the amount of X-ray radiation on the X-ray plane detector during the readout time is determined.

8. An X-ray image diagnostic device comprising an X-ray source for irradiating X-rays onto an object to be examined, an X-ray plane detector placed opposite to the X-ray source for outputting X-rays transmitted through the object as X-ray image data, image storage means for storing X-ray image data output from the X-ray plane detector as digital data, sensitivity correcting means for correcting sensitivity of the X-ray image data stored in the image storage means and for storing sensitivity corrected X-ray image data in the image storage means again, sensitivity-information-acquisition controlling means for commanding that X-ray irradiation from the X-ray source be synchronized with readout of X-ray image data from the X-ray plane detector, sensitivity-information calculating means for calculating sensitivity information for each readout channel of the X-ray plane detector out of the readout X-ray image data, sensitivity-information storing means for storing sensitivity information calculated by said calculating means for correcting sensitivity of the X-ray image data by said sensitivity correcting means.

* * * * *